United States Patent [19]

Hoffmeister et al.

[11] Patent Number: 4,518,355
[45] Date of Patent: May 21, 1985

[54] DENTAL HANDPIECE

[75] Inventors: Jürgen Hoffmeister; Bernhard Kuhn, both of Biberach, Fed. Rep. of Germany

[73] Assignee: Kaltenbach & Voigt GmbH & Co., Biberach, Fed. Rep. of Germany

[21] Appl. No.: 477,222

[22] Filed: Mar. 21, 1983

[30] Foreign Application Priority Data

Apr. 23, 1982 [DE] Fed. Rep. of Germany ....... 3215219

[51] Int. Cl.³ ............................................. A61C 1/00
[52] U.S. Cl. ...................................... 433/29; 433/126
[58] Field of Search .................. 433/29, 126, 85, 114, 433/131, 132, 103, 105

[56] References Cited

U.S. PATENT DOCUMENTS

| 4,080,737 | 3/1978 | Fleer | 433/126 |
| 4,332,562 | 6/1982 | Schuss et al. | 433/126 |
| 4,398,885 | 8/1983 | Loge et al. | 433/29 |
| 4,403,956 | 9/1983 | Nakaniski | 433/29 |

FOREIGN PATENT DOCUMENTS

| 15659 | 9/1980 | European Pat. Off. | 433/29 |
| 1412622 | 11/1975 | United Kingdom | 433/29 |

Primary Examiner—Robert P. Swiatek
Assistant Examiner—John G. Weiss
Attorney, Agent, or Firm—Scully, Scott, Murphy & Presser

[57] ABSTRACT

There is disclosed a dental handpiece which comprises means at one end of the handpiece to mount a dental implement, a drive train arranged within the handpiece and extending to the implement-end in order to operate the dental implement, a light source arranged within the handpiece, and a light guide extending from the light source to a position adjacent to the implement-end of the handpiece for directing light to a treatment region adjacent to the dental implement, the light guide being arranged within the handpiece and along side the drive train.

10 Claims, 6 Drawing Figures

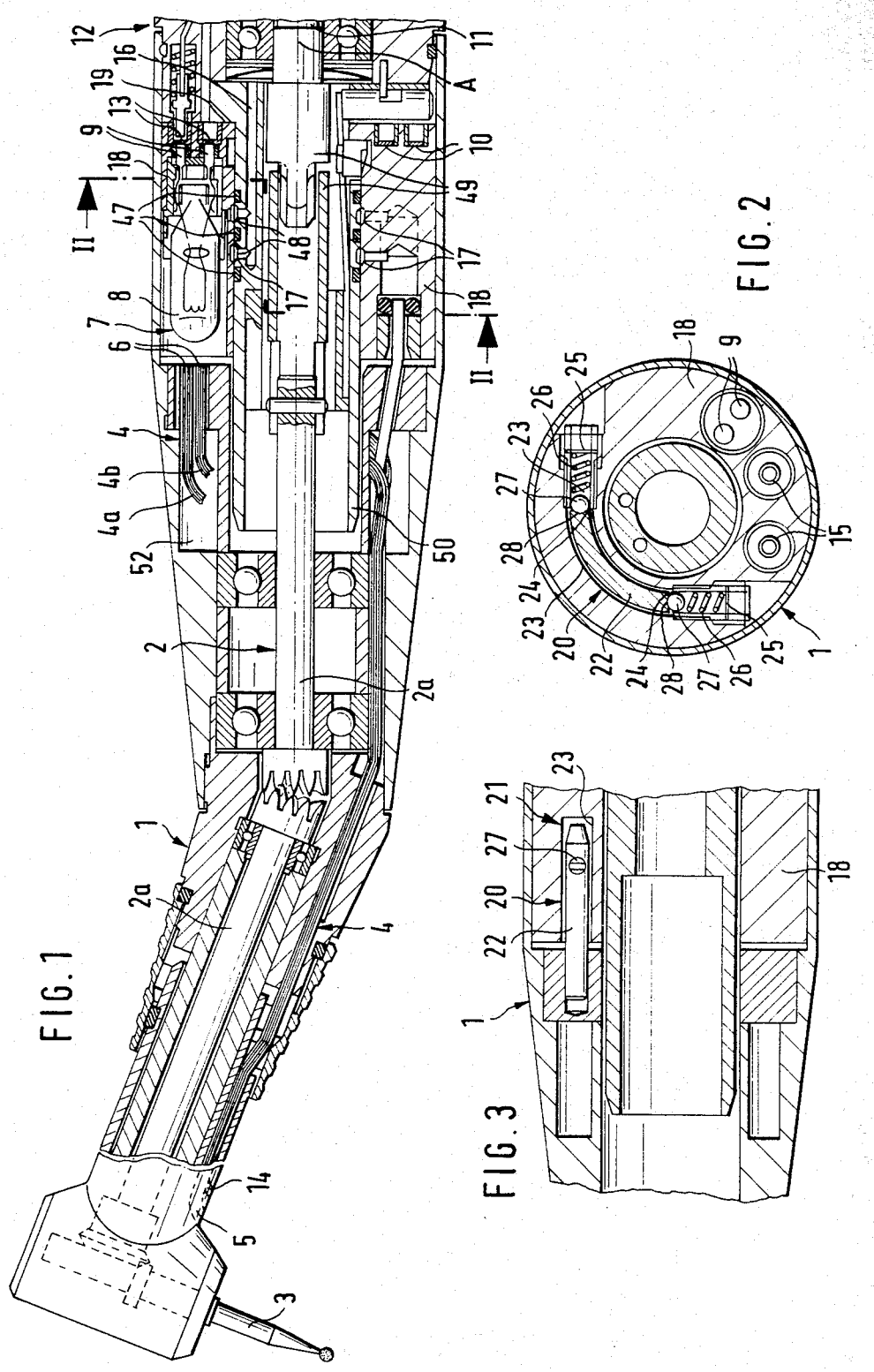

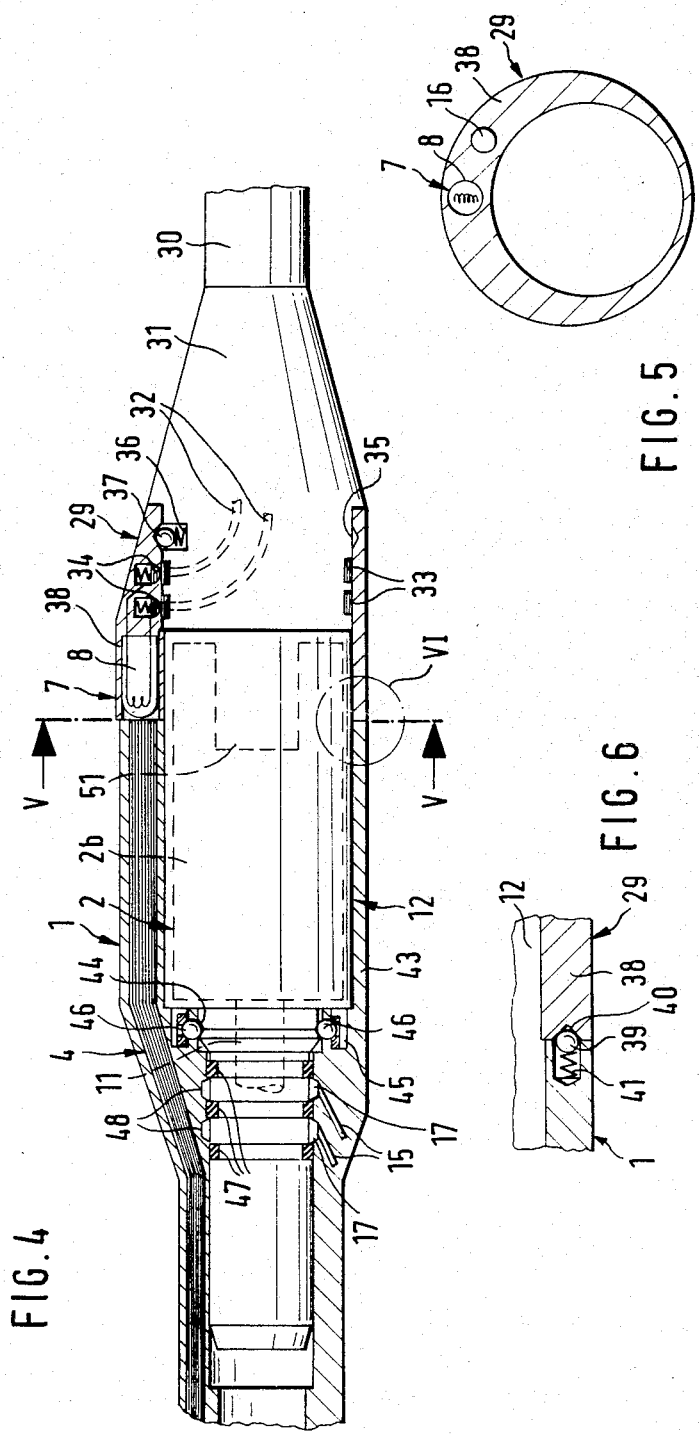

DENTAL HANDPIECE

This invention relates to a straight or angular dental handpiece having means provided at one end of the handpiece to mount a dental implement, a drive train arranged within the handpiece and extending to the implement-end of the handpiece to operate the dental implement, a light source, and a light guide extending from the light source to a position adjacent to the implement-end of the handpiece for directing light to a treatment region adjacent to the dental implement.

BRIEF DESCRIPTION OF THE PRIOR ART

A handpiece of the above general kind is known from German Gebrauchsmuster No. 69 40 204. In this known handpiece a fibre-optic light guide runs inside a flexible hose, which also contains media lines for water and/or air, from one supply member, which is arranged at the end of the handpiece remote from the tool, on the outside along the handpiece as far as the tool end of the handpiece. For the purpose of rendering possible a partially mutual torsion between handpiece and supply member the hose has a certain overlength. The picking-up and holding of the handpiece and also its handling in respect of the patient is made very difficult, in that the hose runs on the outside on the handpiece.

From the advertising pamphlet Hp-018G-0680-20M of the firm American Midwest a dental handpiece of another type is known—namely without mechanical driving elements extending over the length of the handpiece, but with a turbine provided at one end with an inserted tool and with a driving air line, which is arranged therein and which leads from the end of the handpiece remote from the tool to the turbine—in the case of which the fibre-optic light guide is installed into the handpiece. This installation of the fibre-optic light guide into the handpiece is only possible because the driving air line found inside the handpiece is comparatively thin and for this reason sufficient space is present for accommodating the fibre-optic light guide. The situation is completely different in the case of a handpiece of the kind with which the invention is exclusively concerned, in which the comparatively thick mechanical driving elements of the drive train, with their associated mountings, preclude the installation of a fibre-optic light guide.

OBJECT OF THE INVENTION

The invention seeks to provide a dental handpiece of the general kind referred to above i.e having a drive train extending within the handpiece, in which the arrangement of a light guide (which conveys light to a dental treatment region adjacent to the dental implement) is such that the light guide does not provide any hindrance or difficulties in manipulating the handpiece in service.

According to the invention there is provided a dental handpiece comprising means provided at one end of the handpiece to mount a dental implement, a drive train arranged within the handpiece and extending to said one end of the handpiece to operate the dental implement when the latter is mounted on the handpiece, a light source, and a light guide extending from the light source to a position adjacent to said one end of the handpiece for directing light to a treatment region adjacent to the dental implement, said light guide being arranged within the handpiece and alongside the drive train.

The advantages which can be achieved with a dental handpiece according to the invention can essentially be seen to reside in the feature that the light guide, which is arranged inside the handpiece alongside the drive train without requiring any large amount of space, does not cause any hindrance or difficulties in picking-up and holding the handpiece (which has mechanical driving elements of a drive train arranged within it). Also, ready manipulation of the handpiece is not impeded by the light guide, as is the case with known constructions of dental handpiece having an internally mounted drive train.

Embodiments of the invention will now be described in detail, by way of example only, with reference to the accompanying drawings.

BRIEF DESCRIPTION OF THE DRAWINGS

FIG. 1 is a sectional view of a first embodiment of dental handpiece according to the invention;

FIG. 2 is a section taken on the line II—II in FIG. 1;

FIG. 3 is a cutaway section of the handpiece according to FIG. 1 in a sectional plane twisted in respect of FIG. 1;

FIG. 4 is a sectional view of a modification to the embodiment of FIG. 1;

FIG. 5 is a section taken on the line V—V in FIG. 4; and

FIG. 6 is an enlarged illustration of the circled item VI in FIG. 5.

DESCRIPTION OF THE PREFERRED EMBODIMENTS

Referring now to FIGS. 1 to 3, a dental handpiece 1 has mechanical driving elements 2, which form part of a drive train arranged therein and which extends essentially over the length of the handpiece, and comprise a driving shaft 2a, which serves the purpose of operating (in the case of FIG. 1 of rotating) a dental implement or tool 3, for example a drill. Means is provided at one end of the handpiece to mount any desired dental implement. A driving motor 2b (see FIG. 4) is connected with the driving shaft 2a by way of a drive shaft 11, which can be coupled therewith, and which can be formed, for example, by an electric motor, a fluid-operated motor or a rotating piston air motor.

Furthermore, the handpiece 1 is provided with a fibre-optic light guide 4 (of clustered fibres made of glass, synthetic material or the like) whose end 5, which is located at the tool end of the handpiece, is directed towards a treatment region adjacent to the tool 3 and whose light-receiving end 6, which is remote from the tool, faces a light source 7.

The fibre-optic light guide 4 and the light source 7 are arranged eccentrically (off-centre), that is by the side of the mechanical driving elements 2 of the drive train, and inside the handpiece 1.

The light source 7 consists of an electrically energisable incandescent lamp 8, the electrical current supplies 9 of which according to FIGS. 1 to 3 also run inside the handpiece 1 and terminate, at a second end of the handpiece remote from the tool, via first contacts 10. At the second end of the handpiece 1 remote from the tool there can be coupled a driving member 12 which incorporates the drive shaft 11, to be engaged with the driving shaft 2a (which forms part of the driving train elements 2), by means of a coupling element 49. The driving member 12 has second contacts 13 working together with the contacts 10 of the handpiece 1. In the coupled state the handpiece 1 and the driving member 12 are freely counter-rotatable about the longitudinal axis A of the handpiece, the contacts 10 and 13 remaining in contact, since at least one of them is constructed as a sliding or annular contact.

It follows from FIGS. 1, 2, 4 and 5 that the fibre-optic light guide 4, which is arranged in the handpiece 1, runs parallel or approximately parallel to one or several media delivery lines 15 (whose tool end 14 is directed towards the treatment-region of the tool 3), which are arranged in the handpiece and to which there are co-ordinated supply media lines 16 which are arranged in the driving member 12. Communication is established between the lines 15 and 16 by communication means comprising media line crossovers 17 between handpiece 1 and driving member 12, for all relative rotational positions of the handpiece 1 and driving member 12. This is achieved with the aid of annular seals 47, which are known as such, in interaction with annular channels 48.

In the embodiment according to FIGS. 1 to 3, the light source 7 is arranged in an annular insert 18 which can be inserted into the handpiece 1 from the end of the handpiece remote from the tool so that it is secure against rotation, which surrounds the driving shaft 2 and/or the drive shaft 11 and which has the contacts 10 of the handpiece 1 in its front wall 19 remote from the tool. Co-operating latching elements are provided for the purpose of locating the insert 18 so that it is secure against rotation. Thus, the handpiece 1 has a latching member 20, which is eccentric, i.e. is arranged by the side of the driving elements 2, and which extends in the direction of the longitudinal axis A of the handpiece to the insert 18, while the insert 18 has a latch-engaging member 21 which can be engaged with the member 20 and which is arranged at the same radius as the latter.

As FIGS. 2 and 3 show, the member 20 consists of a shell 22, which partially surrounds the driving shaft 2 and/or the drive shaft 11, and the member 21 consists of a slot 23 which receives the shell 22 and is adapted to the shell with regard to shape and size. The shell 22 has a curve which runs along a circular path and which extends through an arc subtending approximately 90°. Furthermore, the shell 20—as indicated in FIG. 3—can be firmly inserted into the handpiece 1, for example with press-fit. The shell 22 engages into the slot 23 in a reslient manner. In addition to this, between both ends 24 of the shell 22, which run in the longitudinal direction of the handpiece 1, that is in the direction of the longitudinal axis A of the handpiece, and the base 25 of the slot 23, which is coordinated with the respective end edge and which is at a distance from this end edge, there are arranged in each case one or several compression springs 26. The springs 26 act, by way of one or several stop balls 27, on the respective end 24, in the case of which the latter have stop recesses 28 which co-operate with the stop balls 27.

In the embodiment according to FIGS. 4 to 6 there is provision for the incandescent lamp 8 (forming the light source 7) in an extension piece 29 which is arranged so that it is secure against rotation in respect of the handpiece 1. The extension piece 29 is connected—in a freely rotating manner about the longitudinal axis A of the handpiece—with a supply member 31, which has a connecting supply hose 30, preferably arranged so that it is detachable. The supply member 31 contains electrical current supplies 32 which come from the supply hose 30 and which work together with contacts 34 of the extension piece which are coordinated with the incandescent lamp 8, the contacts 33 and/or 34 being constructed as sliding or annular contacts.

The connections in FIGS. 1 to 6 between handpiece 1 and driving member 12 and also, in FIGS. 4 to 6, if necessary, between driving member 12 and supply member 31 are preferably constructed as so-called in-line quick couplings. For this the driving member 12 has a plug-in spigot 50 and the supply member 31 has a plug-in spigot 51 which is inserted in each case into the end of the connecting member 1 or 12 remote from the tool in a latching manner.

The extension piece 29 is constructed as a ring surrounding the tool end of the supply member 31, and a spring loaded latching arrangement is provided to maintain axially the connection together of the extension piece 29 and the supply member 31. Thus, the ring, which forms the extension piece 29, has on its inner wall an annular groove 35 into which one or several stop bodies 37, for example balls, which are pressed outwards under the impact of a spring 36 and which are mounted in the outer wall of the supply member 31, can be engaged.

From FIGS. 4 to 6 it follows, moreover, that the ring, which forms the extension piece 29, has an extension 38 which extends beyond the tool end of the supply member 31 and contains the incandescent lamp 8. Also, extension 38 surrounds the end, (which is remote from the tool), of the driving member 12 which contains the driving motor 2b belonging to the driving elements 2. The motor 2b is inserted into the end of the handpiece 1 which is remote from the tool, but projects from this end of the handpiece and also is surrounded by the extension 38.

A resiliently operated latching arrangement is provided for the purpose of connecting handpiece 1 and extension piece 29 against rotation. Thus, as shown in FIG. 6, there are arranged in both front contacting surfaces, which are turned towards one another, of the named parts 1, 29 latching elements (39,40) which engage into one another in a resilient manner. The latching elements are formed by one or several stop bodies, for example balls 39, for which there is provision in one of the front surfaces and which are pressed towards the other front surface under the impact of a spring 41, and also by one or several stop recesses 40 for which there is provision in the other front surface. As FIG. 4 shows, the section of the annular end portion 43 i.e. the second end of the handpiece remote from the implement-mounting end, which has the fibre-optic light guide 4 (and which surrounds the driving member 12) and also the (widened) portion 38 (which has the incandescent lamp 8) of the ring forming the extension piece 29, are constructed to be widened relative to the adjoining parts.

Furthermore, it follows from FIG. 4 that a spring loaded latching arrangement is provided for the axial security between handpiece 1 and driving member 12. Thus, the latter has on its outer wall one or several stop recesses 44 and the handpiece 1 has on the inner wall of the annular end portion 43, which encompasses the driving member 12, one or several stop bodies 46, for example balls, which engage into the stop recesses 44 under the impact of a spring 45.

The stop recess 44 is constructed as an annular groove into which several balls, which are arranged spaced over the periphery, engage. The spring 45 can be constructed as a resilient annular member.

As is shown more particularly in FIG. 1, the fibre-optic light guide 4 can be divided into two partial fibre-optic light guides 4a, 4b running alongside one another. As, according to FIG. 1, the media lines 15 of the handpiece, which can, for example, be coolant lines, lie diametrically opposite the light source 7 otherwise, however, together, that is, they run adjacent to the fibre-optic light guide 4 inside the handpiece to the tool end of the handpiece, the handpiece 1 has in the proximity of the end of the fibre-optic light guide 4 which is remote from the tool, an annulus 52 which surrounds the driving shaft 2a or the plug-in spigot 50 completely, or e.g. only by halves. Into the annular chamber formed by annulus 52 there extends the light-receiving end region of the fibre-optic light guide 4 as it comes from the light source 8, this end region being diametrically opposed to the housing of the media lines 15 in the annular chamber.

The incandescent lamp 8 may be formed by a lens type electric bulb, though other arrangements of electrically energisable light source may be provided, as desired.

We claim:

1. A dental handpiece comprising means provided at one end of the handpiece to mount a dental implement, a drive train arranged within the handpiece and extending to said one end of the handpiece to operate the dental implement when the latter is mounted on the handpiece, a light source consisting of an electrically energizable incandescent lamp arranged within said handpiece, and a light guide extending from the light source to a position adjacent to said one end of the handpiece for directing light to a treatment region adjacent to the dental implement, said light guide being arranged within the handpiece and extending alongside the drive train, an electrical supply to said incandescent lamp which extends within the handpiece from a second end of the handpiece remote from the implement-end thereof, a first contact for said electrical supply being arranged at said second end of the handpiece, and a second contact for engaging said first contact being connected to a source for said electrical supply, including a driving device, couple with said second end of the handpiece and having a drive shaft engaging with said drive train, and a second contact engaging with said first contact, the driving device and the handpiece being relatively rotatable when coupled together, and said first and second contacts being slidably interengageable.

2. A dental handpiece as claimed in claim 1, including a fluid medium delivery line extending within the handpiece generally parallel to said light guide and terminating near said one end of the handpiece in order to convey a fluid medium to said treatment region, a corresponding fluid medium supply line arranged in said driving member, and communication means provided in the handpiece and in the driving member to communicate said supply line with said delivery line for all relative rotational positions of the handpiece and the driving member.

3. A dental handpiece as claimed in claim 2, including an annular insert non-rotatably located in said second end of the handpiece so as to surround said drive train, said insert being inserted in the handpiece via said second end and having said light source arranged therein, and said first contact being provided in an end wall of the insert remote from the implement-end of the handpiece.

4. A dental handpiece as claimed in claim 3, including co-operating latching elements provided on the handpiece and on said annular insert so as to locate the annular insert non-rotatably in the handpiece.

5. A dental handpiece as claimed in claim 4, in which the latching element on the handpiece comprises an arcuate shell which partly surrounds the drive train, and the latching element on said annular insert comprises an arcuate slot arranged to receive said shell.

6. A dental handpiece as claimed in claim 5, in which said shell and said slot have a resilient interengagement.

7. A dental handpiece as claimed in claim 6, including a spring arranged at least one end of the slot to engage with an adjacent end of the shell.

8. A dental handpiece as claimed in claim 7, including a stop member arranged to be pressed by said spring against the adjacent end of the shell.

9. A dental handpiece comprising means provided at one end of the handpiece to mount a dental implement, a drive train arranged within the handpiece and extending to said one end of the handpiece and extending to said one end of the handpiece to operate the dental implement when the latter is mounted on the handpiece, a light source consisting of an electrically energizable incandescent lamp arranged within said handpiece, and a light guide extending from the light source to a position adjacent to said one end of the handpiece for directing light to a treatment region adjacent to the dental implement, said light guide being arranged within the handpiece and extending alongside the drive train, an electrical supply to said incandescent lamp with extends within the handpiece from a second end of the handpiece remote from the implement-end thereof, a first contact for said electrical supply being arranged at said second end of the handpiece, and a second contact for engaging said first contact being connected to a source for said electrical supply, including a driving device, coupled with said second end of the handpiece and having a drive shaft engaging with said drive train, and a second contact engaging with said first contact, and in which the driving device and the handpiece are relatively rotatable when coupled together, and said first and second contacts are slidably interengageable, and including a fluid medium delivery line extending with the handpiece generally parallel to said light guide and terminating near said one end of the handpiece in order to convey a fluid medium to said treatment region, a corresponding fluid medium supply line arranged in said driving member, and communication means provided in the handpiece and in the driving member to communicate said supply line with said delivery line for all relative rotational positions of the handpiece and the driving member, including an annular insert non-rotatably located in said second end of the handpiece so as to surround said drive train, said insert being inserted in the handpiece via said second end and having said light arranged therein, and said first contact being provided in an end wall of the insert remote from the implement-end of the handpiece, and including a detachable extension which mounts said light and which is non-rotatably securable to the handpiece, and a supply member rotatably connected at one end to said extension, a supply tube connected to said member, an electrical supply line provided in said supply tube, a first contact provided on said extension, and a second contact provided on said supply member and engaging with said first contact to provide electrical power to operate said light, said first and second contacts being slidably interengageable, and in which said extension is annular and surrounds said one end of the supply member, and including a spring-loaded latch arrangement for axially maintaining said extension and said supply member connected together.

10. A dental handpiece as claimed in claim 9, including a driving device received within the handpiece and comprising a drive motor coupled with said drive train, said driving device being inserted in the handpiece via said second end thereof with an end of the driving device projecting from said second end of the handpiece, and said annular extension surrounding said projecting end of the driving device, and in which said second end of the handpiece is widened relative to the remainder of the handpiece, including a widened portion of said annular extension in which said light is mounted, and including a spring-loaded latching arrangement for maintaining the driving device and the handpiece axially located together, said latching device acting between an inner wall of the handpiece in which the driving device is received and the driving device and comprising spring urged latching elements engageable in latching recesses.

* * * * *